United States Patent [19]

Hazato et al.

[11] Patent Number: 5,149,711
[45] Date of Patent: Sep. 22, 1992

[54] 2-CYCLOPENTENONE DERIVATIVES

[75] Inventors: Atsuo Hazato, Hino; Seizi Kurozumi, Kokubunji, both of Japan

[73] Assignee: Teijin Limited, Osaka, Japan

[21] Appl. No.: 319,688

[22] Filed: Mar. 7, 1989

[30] Foreign Application Priority Data

Mar. 9, 1988 [JP] Japan .................................. 63-53681

[51] Int. Cl.$^5$ ..................... A61K 31/12; A61K 31/22; C07C 49/747; C07C 69/21
[52] U.S. Cl. .................................. 514/548; 514/546; 514/552; 514/684; 514/690; 556/441; 560/231; 560/255; 568/330; 568/379
[58] Field of Search ................ 560/255, 231; 514/546, 514/548, 684, 690, 552; 568/330, 379

[56] References Cited

U.S. PATENT DOCUMENTS

| | | | |
|---|---|---|---|
| 4,560,703 | 12/1985 | Fukushima et al. | 514/530 |
| 4,711,895 | 12/1987 | Hazato et al. | 514/530 |

FOREIGN PATENT DOCUMENTS

| | | |
|---|---|---|
| 0104631 | 4/1984 | European Pat. Off. |
| 0180399 | 5/1986 | European Pat. Off. |
| 60-97926 | 5/1985 | Japan . |
| 62-96438 | 5/1987 | Japan . |
| 1022865 | 3/1966 | United Kingdom . |

OTHER PUBLICATIONS

Nagaoka et al., Tetrahedron Letters, vol. 26, No. 41, pp. 5053-5056.
Smith et al., Tetrahedron Letters, vol. 21, No. 49 (1980) pp. 4691-4694.

*Primary Examiner*—Vivian Garner
*Attorney, Agent, or Firm*—Wenderoth, Lind & Ponack

[57] ABSTRACT

A 2-cyclopentenone derivative represented by the following formula

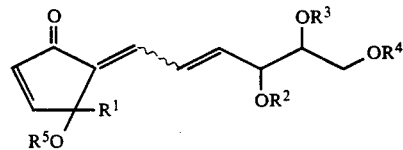

wherein $R^1$ represents an alkyl group having 1 to 10 carbon atoms which may be substituted by a substituted or unsubstituted phenyl or phenoxy group, $R^2$, $R^3$, $R^4$ and $R^5$ are identical or different and each represents a hydrogen atom or a lower alkanoyl group, and the wavy line shows that the bonded state of the double bond is E or Z.

This compound is useful for treating, for instance, malignant tumors.

7 Claims, No Drawings

2-CYCLOPENTENONE DERIVATIVES

This invention relates to novel 2-cyclopentenone derivatives, and more specifically, to cyclopentenone derivatives represented by the following formula

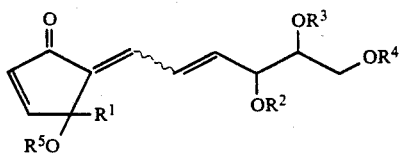

wherein $R^1$ represents an alkyl group having 1 to 10 carbon atoms which may be substituted by a substituted or unsubstituted phenyl or phenoxy group, $R^2$, $R^3$, $R^4$ and $R^5$ are identical or different and each represents a hydrogen atom or a lower alkanoyl group, and the wavy line shows that the bonded state of the double bond is E or Z,
and their use as medicaments, particularly as drugs for treating malignant tumors.

The present inventors and their coworkers previously found that 4-hydroxy-2-cyclopentenones of the formula

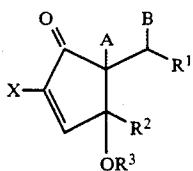

wherein X represents a hydrogen or halogen atom, A represents a hydrogen atom and B represents a hydroxyl group, or A and B are bonded to each other to represent a bond, $R^1$ represents a substituted or unsubstituted alkyl, alkenyl or alkynyl group having 1 to 10 carbon atoms, $R^2$ represents a substituted or unsubstituted alkyl, alkenyl or alkynyl group having 1 to 10 carbon atoms, and $R^1$ represents a hydrogen atom or a protective group for the hydroxyl group, provided that $R^2$ is not a 2-octenyl, 8-acetoxy-2-octenyl or 2,5-octadienyl group,
were useful for the treatment of malignant tumors, and disclosed it in U.S. Pat. No. 4,711,895 (corresponding to European Patent Publication No. 180,399).

The above U.S. Patent broadly discloses many compounds embraced by formula (A), but does not specifically disclose 2-cyclopentenone derivatives of formula (I) in which three hydroxyl groups and/or lower alkanoyloxy groups are bonded to specific sites on the alpha-chain.

The present inventors studied the pharmacological properties of the compounds of formula (A) previously disclosed and related compounds, and have now found that the compounds of formula (I) above provided by this invention have lower toxicity and much higher pharmacological activity, particularly suppressing activity on malignant tumors, than the compounds of a similar structure specifically disclosed in the above-cited U.S. Patent.

In the present specification and the appended claims, the term "lower" means that a group or compound qualified by this term has not more than 10, preferably 5, carbon atoms.

The alkyl group represented by $R^1$ in formula (I) may be linear or branched, and include, for example, methyl, ethyl, n-propyl, iso-propyl, n-butyl, sec.-butyl, tert-butyl, n-pentyl, n-hexyl, n-heptyl, n-octyl, n-nonyl and n-decyl.

Of these, alkyl groups having 3 to 8 carbon atoms ar preferred.

The alkyl groups may be substituted optionally by a substituted or unsubstituted phenyl or phenoxy group. Substituents which may exist on the benzene ring in the substituted phenyl or phenoxy group include lower alkyl groups and lower alkoxy groups. The benzene ring may be substituted by 1 to 3, preferably 1 or 2, such substituents.

Specific examples of alkyl groups substituted by a substituted or unsubstituted phenyl or phenoxy group include phenylmethyl, phenylethyl, phenylbutyl, 3,4-dimethoxyphenylbutyl, phenoxymethyl, phenoxyethyl, phenoxypropyl and phenoxybutyl.

Of these, the phenoxybutyl group is preferred.

Examples of the lower alkanoyl group represented by $R^2$, $R^3$, $R^4$ and/or $R^5$ include acetyl, propanoyl, butynoyl and pentanoyl.

Of these, the acetyl group is preferred.

Typical examples of the compounds of formula (I) provided by this invention are given below.

(1) 5-(4,6-diacetoxy-5-hydroxy-2-hexenyl-idene)-4-phenoxybutyl)-4-hydroxy-2-cyclopentenone (2) 5-(4S,5R)-4,6-diacetoxy-5-hydroxy-2-hexenylidene)]-4-(4-phenoxybutyl)-4-hydroxy-2-cyclopentenone (3) 5-(4,5,6-trihydroxy-2-hexenylidene)-4-(4-phenoxybutyl)-4-hydroxy-2-cyclopentenone (4) 5-[(4S,5R)-4,5,6-trihydroxy-2-hexenylidene-4-(4-phenoxybutyl)-4-hydroxy-2-cyclopentenone (5) 5-(4,5,6-triacetoxy-2-hexenylidene)-4-(4-phenoxybutyl)-4-hydroxy-2-cyclopentenone (6) 5-(4S,5R)-4,5,6-triacetoxy-2-hexenylidene]-4-(4-phenoxybutyl)-4-hydroxy-2-cyclopentenone (7) 5-(4,6-diacetoxy-5-hydroxy-2-hexenylidene)-4-3-(3,4-dimethoxyphenyl)propyl)-4-hydroxy-2-cyclopentenone (8) 5-(4,5,6-trihydroxy-2-hexenylidene)-4-3-( 3,4-dimethoxyphenyl)propyl]-4-hydroxy-2-cyclopentenone (9) 5-(4,5,6-triacetoxy-2-hexanylidene)-4-[3-(3,4-dimethoxyphenyl)propyl)-4-hydroxy-2-cyclopentenone

(10) 5-(4,6-diacetoxy-5-hydroxy-2-hexenyl-idene)-4-hydroxy-2-cyclopentenone

(11) 5-(4,5,6-trihydroxy-2-hexenylidene)-4-octyl-4-hydroxy-2-cyclopentenone

(12) 5-(4,5,6-triacetoxy-2-hexenylidene)-4-octyl-4-hydroxy-2-cyclopentenone

(13) 5-(4,6-diacetoxy-5-hydroxy-2-hexenyl-idene)-4-butyl-4-hydroxy-2-hexenylidene)-4-butyl-4-hydroxy-2-cyclopentenone

(14) 5-(4,5,6-trihydroxy-2-hexenylidene)-4-butyl-4-hydroxy-2-cyclopentenone

(15) 5-(4,5,6-triacetoxy-2-hexenylidene)-4-butyl-4-hydroxy-2-cyclopentenone

(16) 5-(4,6-diacetoxy-5-hydroxy-2-hexenyl-idene)-4-(3-phenylpropyl)-4-hydroxy-2-cyclopentenone

(17) 5-(4,5,6-trihydroxy-2-hexenylidene)-4-(3-phenylpropyl)-4-hydroxy-2-cyclopentenone

(18) 5-(4,5,6-triacetoxy-2-hexenylidene)-4-(3-phenylpropyl)-4-hydroxy-2-cyclopentenone Especially preferred are compounds of the following formulae.

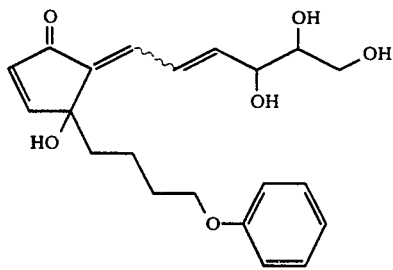

(I-a)

and

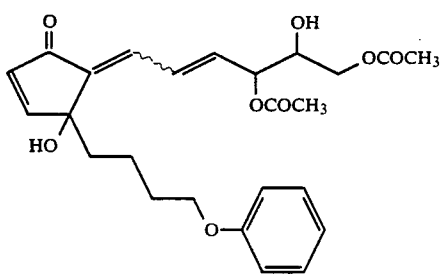

(I-b)

The compound of formula (I) provided by this invention can be produced, for example, by subjecting a cyclopentenone represented by the following formula

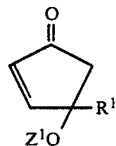

(II)

wherein $Z^1$ represents a protective group for the hydroxyl group, $R^1$ is as defined above, to aldol condensation reaction with an aldehyde represented by the following formula

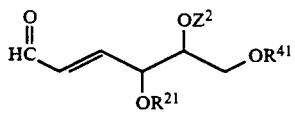

(III)

wherein $R^{21}$ and $R^{41}$ are identical or different and each represents a lower alkanoyl group, and $Z^2$ represents a protective group for the hydroxyl group, dehydrating the resulting compound of the formula

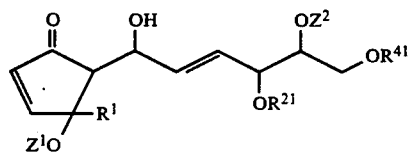

(IV)

wherein $R^1$, $R^{21}$, $R^{41}$, $Z^1$ and $Z^2$ are as defined above, to form a compound represented by the formula

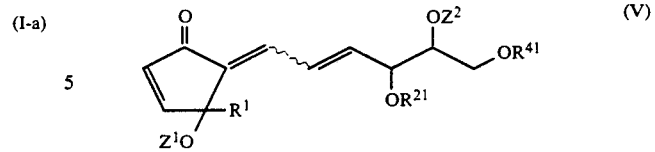

(V)

wherein $R^1$, $R^{21}$, $R^{41}$, $Z^1$ and $Z^2$ are as defined above, then splitting off the protective groups $Z^1$ and $Z^2$, and as required, splitting off one or more lower alkanoyl groups which exist, or lower alkanoylating one or more free hydroxyl groups which may exist.

In the formula (II) or (III) above, the protective group $Z^1$ or $Z^2$ for the hydroxyl group may be any desired hydroxy-protective groups, and include, for example, tri($C_1$–$C_7$)hydrocarbon-silyl groups which can be easily split off by acidic hydrolysis and groups which form an acetal linkage with the oxygen atom of the hydroxyl group.

Specific examples of preferred tri($C_{1-7}$ hydro-carbon)silyl groups include tri($C_{1-4}$ alkyl)silyl groups such as trimethylsilyl, triethylsilyl or t-butyldimethylsilyl, diphenyl($C_{1-4}$ alkyl)silyl groups such as t-butyldiphenylsilyl, and a tribenzylsilyl group.

Examples of the groups forming an acetal linkage together with the oxygen atom of the hydroxyl group include methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl and 6,6-dimethyl-3-oxa-2-oxo-bicyclo3.1.0-)hex-4-yl groups. Of these, 2-tetrahydropyranyl, 2-tetrahydrofuranyl, 1-ethoxyethyl, 2-methoxy-2-propyl, (2-methoxyethoxy)-methyl and 6,6-dimethyl-3-oxa-2-oxo-bicyclo3.1.0)-hex-4-yl groups are particularly preferred.

In the process mentioned above, the compound of formula (II) and the compound of formula (III) are first subjected to aldol condensation. The aldol condensation reaction is carried out in a solvent in the presence of a basic compound. Compounds suitably used as the basic compound and the reaction solvent are, for example, those described in A. T. Nielsen, W. J. Houlihan: Org. React., 16, 1 (1968); H. 0. House, "Modern Synthetic Reactions", 2nd edition, Benjamin (1972), p. 629; and Shin Jikken Kagaku Koza, 14, II 736, III 851.

In the aldol condensation reaction, a dialkylboron trifluoromethanesulfonate such as dibutylboron trifluoromethanesulfonate is used as a condensation agent in the presence of a metal amide such as lithium diisopropyl amide, lithium diethyl amide or lithium bistrimethylsilyl amide or a tertiary amine such as triethylamine, diisopropylethylamine or triethylbutylamine.

When the aldol condensation reaction is carried out by using the metal amide, the amount of the metal amide is, for example, 0.3 to 30 equivalents, preferably 0.9 to 10 equivalents, relative to the compound of formula (II). Examples of the reaction solvent are ethers such as diethyl ether or tetrahydrofuran, and hydrocarbons such as petroleum ether, hexane and pentane. The reaction temperature is preferably −100 to 50 ° C., especially preferably −80 to 0 ° C.

When the aldol condensation reaction is carried out in the presence of the tertiary amine using the dialkylboron trifluoromethanesulfonate, the amount of each of these compounds used is, for example, 0.5 to 50 equivalents, preferably 1 to 10 equivalents, relative to the compound of formula (II).

The amount of the aldehyde of formula (III) as the other starting material is, for example, 0.5 to 10 equivalents, preferably 0.8 to 2 equivalents, relative to the compound of formula (II).

The reaction time varies depending upon the types of the starting compounds, the reagents, the reaction solvent used. Usually, it is 5 minutes to 24 hours, preferably 10 minutes to 12 hours.

After the reaction, the product of formula (IV) can be purified and recovered by usual means such as extraction, washing with water, drying and chromatography.

The resulting compound of formula (IV) is subjected to dehydration reaction. The dehydration reaction is carried out preferably by using a basic compound and a reactive derivative of an organic sulfonic acid. Specifically, it is preferred to treat the compound of formula (IV) first with the basic compound and the reactive derivative of an organic sulfonic acid, and then treating the product further with the basic compound. First, the hydroxyl group of the compound of formula (IV) is sulfonylated, and then split off as an organic sulfonic acid, whereupon the dehydration reaction is completed.

Amines are preferred as the basic compound used together with the derivative of an organic sulfonic acid. Examples of the amines include pyridine, 4-dimethyl-aminopyridine, triethylamine, diisopropylcyclohexylamine, 1,5-diazabicyclo[4.3.0]non-5-ene (DBN for short), 1,8-diazabicyclo5.4.0]undec-7-ene (DBU for short), quina-cridine, triethylenediamine, isopropyldimethylamine and diisopropylethylamine. Of these, pyridine, 4-dimethyl-aminopyridine, DBU and DBN are preferred.

Examples of the reactive derivative of organic sulfonic acid include organic sulfonic acid halides such as methanesulfonyl chloride, ethanesulfonyl chloride, n-butanesulfonyl chloride, t-butanesulfonyl chloride, trifluoromethanesulfonyl chloride, benzenesulfonyl chloride and p-toluenesulfonyl chloride; and organic sulfonic acid anhydrides such as methanesulfonic anhydride, ethanesulfonic anhydride, trifluoromethanesulfonic anhydride, benzenesulfonic anhydride and p-toluenesulfonic anhydride.

The above basic compounds themselves may be used as a solvent for the reaction. Other examples of the solvent include halogenated hydrocarbons such as dichloromethane, chloroform, carbon tetrachloride and dichloroethane; ethers such as diethyl ether and tetrahydrofuran; and hydrocarbons such as benzene, toluene, pentane, hexane and cyclohexane. Pyridine and dichloromethane are preferred.

The amount of the derivative of an organic sulfonic acid is preferably 1 to 10 equivalents per mole of the compound of general formula (IV).

The amount of the basic compound is at least 1 equivalent, preferably at least 2 equivalents, relative to the above reactive derivative of an organic sulfonic acid.

The amount of the solvent used is usually 1 to 1000 times, preferably 5 to 100 times, the volume of the compound of formula (IV).

The reaction temperature varies depending upon the starting compound, the basic compound, solvent, etc., and is usually −10° C. to 50° C., preferably 0 to 30° C. The reaction time varies over a wide range depending upon various conditions, and is about 0.1 to 10 hours. The progress of the reaction can be monitored, for example, by thin-layer chromatography.

Thus, as a result of the above reaction (to be referred to as the first reaction), an organic sulfonyloxy derivative of the cyclopentenone of formula (IV) is formed by the conversion of the hydroxyl group on the 5-position alkyl group into an organic sulfonyloxy group. The resulting compound is then reacted with the basic compound (to be referred to as the second reaction) to split off the corresponding organic sulfonic acid and thus converted to a 4-hydroxy-2-cyclopentenone represented by the following formula (V).

Examples of the basic compound that can be used in the second reaction may be the same as those given hereinabove with regard to the basic compound used in the first reaction. The basic compound used in the second reaction may be different from that used in the first reaction.

The second reaction can be carried out at the same temperature. The organic sulfonyloxy derivative formed in the first reaction may be subjected to the second reaction after isolating it or in the same reaction system as in the first reaction. After the reaction, the desired compound is purified and recovered by usual means.

The protective groups $Z^1$ and $Z^2$ are split off from the compound of formula (V) thus obtained. Elimination of the hydroxyl-protective group can be carried out by the following method.

When the protective group forms an acetal linkage together with the oxygen atom of the hydroxyl group, the deprotection reaction is carried out, for example, by using acetic acid, a pyridinium salt of p-toluenesulfonic acid or a cation exchange resin as a catalyst and water, tetrahydrofuran, ethyl ether, dioxane, acetone or acetonitrile as a solvent. The reaction is carried out usually at a temperature of −78 to +30° C. for a period of about 10 minutes to about 3 days.

When the protective group is a tri($C_1$–$C_7$)-hydrocarbon-silyl group, the deprotection reaction is carried out at the same temperature as above in the above-exemplified reaction solvent in the presence of acetic acid, tetrabutyl ammonium fluoride, cesium fluoride, etc.

By this reaction of eliminating the protective groups for the hydroxyl groups, a compound of the following formula

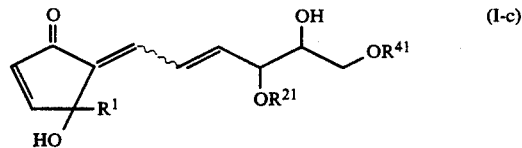

(I-c)

wherein $R^1$, $R^{21}$ and $R^{41}$ are as defined above, is obtained. As required, one or more lower alkanoyl groups ) that exist may be split off, or one or more free hydroxyl groups that exist in the compound resulting from elimination of the lower alkanoyl groups may be lower alkanoylated.

Elimination of the lower alkanoyl groups may usually be carried out by hydrolysis. Hydrolysis may be carried out by using an enzyme such as lipase in water or an aqueous solution at a temperature of −10° C. to +60° C. for a period of about 10 minutes to 24 hours.

The lower alkanoylation of the free hydroxyl groups may be carried out by a known method. For example, it can be carried out by reaction with a reactive derivative, such as a halide or anhydride, of a lower alkanoic acid, preferably in the presence of a basic compound.

The compounds of formula (I) provided by this invention are markedly characterized by having the excellent activity of suppressing the proliferation of malignant tumors, and lower cytotoxicity than the compounds of a similar structure disclosed specifically in the above-cited U.S. Pat. No. 4,711,895, and are useful as a drug for treating cancer.

The excellent pharmacological properties of the compounds of this invention can be demonstrated by the following in vitro and in vivo experiments.

(1) Measurement of the action of inhibiting Proliferation of L1210 leukemia cell L1210 leukemia cells were added to an RPMI medium containing 10% FCS (fetal calf serum), and the concentration of the cells was adjusted to $1 \times 10^5$ cells/min. Each of the test compounds shown in Table I was dissolved in 99.5% ethanol. Prior to use, the final concentration of the ethanol solution was adjusted to less than 0.1%, and it was added to the culture medium. The culture medium was then maintained at 37° C. in a stationary condition for 4 days. After the cultivation, the number of surviving cells was measured by dyeing with trypan blue. As a control, 0.1% ethanol was used. A dose-reaction curve plotted from the ratios of proliferation against the control, and $IC_{50}$ was determined.

The results are shown in Table I.

TABLE I

| Test compound | $IC_{50}$ (micrograms/ml) |
|---|---|
| 5-[(4S,5R)-4,6-diacetoxy-5-hydroxy-2-hexenylidene]-4-(phenoxybutyl)-4-hydroxy-2-cyclopentenone | 0.2 |
| 5-[(4S,5R)-4,5,6-trihydroxy-2-hexenylidene]-4-(4-phenoxybutyl)-hydroxy-2-cyclopentenone | 0.8 |
| 5-[(4S,5R)-4,5,6-triacetoxy-2-hexenylidene]-4-(4-phenoxybutyl)-4-hydroxy-2-cyclopentenone | 0.1 |

(2) Measurement of the antitumor effect on P338 mouse leukemia tumor $1 \times 10^6$ P388 mouse leukemia cells were intraperitoneally administered to $BDF_1$ mice. After the lapse of 24 hours, each of the test compounds shown in Table II was intraperitoneally administered to the mice for 9 days. The periods of survival of these animals were examined and the increase of their life span (ILS %) was determined.

The results are shown in Table II.

TABLE II

| Test compound | Dosage (mg/kg/day) | ILS (%) |
|---|---|---|
| 5-[(4S,5R)-4,5,6-trihydroxy-2-hexenylidene]-4-(4-phenoxybutyl)-4-hydroxy-2-cyclopentenone (the compound of the invention) | 20 | 44.9 |
|  | 10 | 32.7 |
|  | 5 | 24.5 |
| 5-[(E)-4,7-dihydroxy-(2E)-heptenylidene]-4-(4-phenoxybutyl)-4-hydroxy-2-cyclopentenone (the compound of Example 25 of U.S. Pat. No. 4,711,895) | 20 | −69.2 |
|  | 10 | 31.2 |
|  | 5 | 21.4 |

(3) Measurement of the antitumor effect on B16 melanoma mouise tumor

For B16 melanoma, $BDF_1$ mice were implanted subcutaneously with 0.2 ml of a 10% tumor homogenate in saline in the left flank. The test compounds were each given intraperitoneally on day 1-9. The activity was assessed by measuring the tumor weight on day 18.

The results are shown in Table III.

TABLE III

| Test compound | Dosage (mg/kg/day) | Proliferation inhibitory rate (%) |
|---|---|---|
| 5-[(4S,5R)-4,6-diacetoxy-5-hydroxy-2-hexenylidene]-4-(4-phenoxybutyl)-4-hydroxy-2-cyclopentenone | 10 | 45.5 |
|  | 5 | 9.6 |
| 5-[(E)-4,7-dihydroxy-(2E)-heptenylidene]-4-(4-phenoxybutyl)-4-hydroxy-2-cyclopentenone (the compound of Example 25 of U.S. Pat. No. 4,711,895) | 10 | 32.7 |
|  | 5 | −13.5 |

The compounds of this invention can be administered orally, or parenterally through, for example, percutaneous, subcutaneous, intramuscular, intravenous, intraarterial and intrarectal routes.

Preparations for oral administration may be in the form of, for example, tablets, pills, granules, powders, solutions, suspensions and capsules.

Tablets may be formulated in a usual manner by using excipients such as lactose, starch, calcium carbonate, crystalline cellulose and silicic acid, binders such as carboxymethyl cellulose, methyl cellulose, potassium phosphate and polyvinyl pyrrolidone, disintegrants such as sodium alginate, sodium hydrogen carbonate, sodium lauryl sulfate and stearyl monoglyceride, moisturizers such as glycerin, absorbents such as kaolin and colloidal silica and lubricants such as refined talc and powdered boric acid. Pills, powders and granules can also be formulated by ordinary methods using the excipients and other carriers mentioned above.

Solutions and suspensions may be formulated by ordinary methods using glycerol esters such as tricaprylin and triacetin, purified water, and alcohols such as ethanol.

Capsules may be formulated by filling the granules, powders or solutions prepared as above into gelatin capsules.

Preparations for percutaneous administration may be in the form of, for example, ointments and creams. Ointments may be formulated in a customary manner using fatty oils such as castor oil, olive oil and vaseline. Creams may be formulated in a customary manner using fatty oils and emulsifying agents such as diethylene glycol and sorbitan fatty acid monoesters.

Injectable preparations formulated in solution or suspension may be used for subcutaneous, intramuscular, intraveous or intraarterial administration. In the preparation of solutions and suspensions, propylene glycol, polyethylene glycol, olive oil, ethyl oleate, ester of iodinated pappy seed oil, etc. may generally be used, and as required, a small amount of an antiseptic, stabilizer, etc. may be added. The injectable preparations can be sterilized by filtration through a bacterial filter and by addition of a bactericide.

The injectable preparations may be used in the form of lipid microspheres.

Ordinary suppositories formulated by using soft gelatin capsules are used for intrarectal administration.

The 2-cyclopentenones of formula (I) as the active ingredients of such pharmaceutical preparations can also be included as inclusion compounds formed with alpha-, beta- and gamma-cyclic dextrins or their methylated cyclic dextrins.

The effective dose of the compounds of this invention varies with the age, sex, condition, etc. of a patient to be treated. It is usually in the range of $10^2$ to $2 \times 10^5$ micrograms/kg/day, preferably in the range of $5 \times 10^2$ to $10^4$ micrograms/kg/day.

As described above in detail, the present invention provides the novel 2-cyclopentenones of formula (I) which are useful as antitumor drugs either by themselves or as antitumor preparations containing them as active ingredients.

The following Examples illustrate the present invention more specifically.

EXAMPLE 1

Synthesis of 5-[(4S,5R)-4,6-diacetoxy-1-hydroxy-5-(1-methoxy-1-methylethyloxy)-2-hexen-1-yl]-4-phenoxybutyl)-4-trimethylsilyloxy-2-cyclopentenone

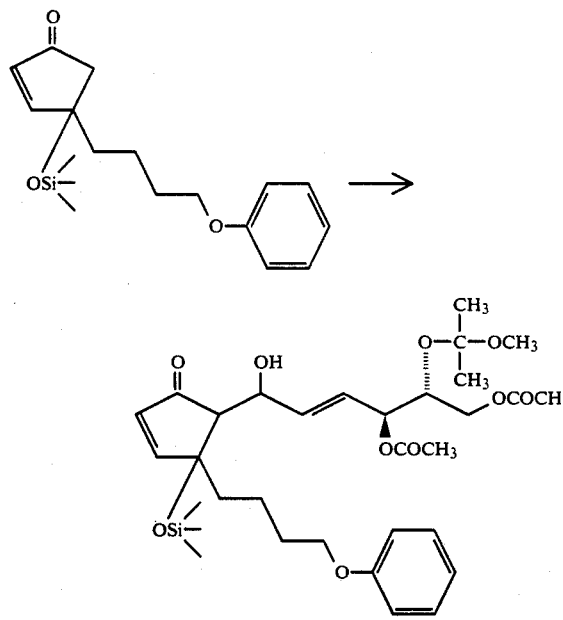

A solution composed of 1 g (3.14 mmoles) of 4-(4-phenoxybutyl)-4-trimethylsilyloxy-2-cyclopentenone, ml of dry hexane and 5 ml of dry ether was cooled to $-78°$ C. under a nitrogen stream, and 767 microliters (4.4 mmoles) of diisopropylethylamine and 4.1 ml of dibutylboron trifurate (lM CH ) was added and the mixture was stirred for 1 hour. Then, 3 ml of a hexane solution of mg (3.14 mmoles) of (4S,5R)-4,6-diacetoxy-5-(1-methoxy-1-methylethyloxy)-2-hexenal was added, and the mixture was stirred for 2 hours. After the reaction, an aqueous solution of ammonium chloride was added to terminate the reaction. The reaction product was extracted with acetic acid, and the organic layer was washed with an aqueous solution of potassium hydrogen sulfate, an aqueous sodium hydrogen carbonate solution and a saturated aqueous solution of sodium chloride in this sequence, and dried over anhydrous magnesium sulfate. The solvent was evaporated under reduced pressure. The resulting oily product was subjected to Florisil column chromatography (hexane/ethyl acetate=5:1→3:1) to give 1.22 g (63%) of an aldol product.

NMR (δppm, CDCl$_3$): 0.12(s, 9H), 1.4(s, 6H), 1.2–2.2(m, 6H), 2.1(s, 6H), 2.62(d, 1H, J=8Hz), 3.3(s, 3H), 3.9–4.35(m, 5H), 4.6(m, 1H), 5.6(m, 1H), 6.0(m, 2H), 6.25(d, 1H, J=6Hz), 6.8–7.1 (m, 3H), 7.2–7.45(m, 2H), 7.66(d, 1H, J=6Hz).

EXAMPLE 2

Synthesis of 5-(4S,5R)-4,6-diacetoxy-5-(1-methoxy-1-methylethyloxy)-2-hexenylidene]-4-(4-phenoxybutyl)-4-trimethylsilyloxy-2-cyclopentenone

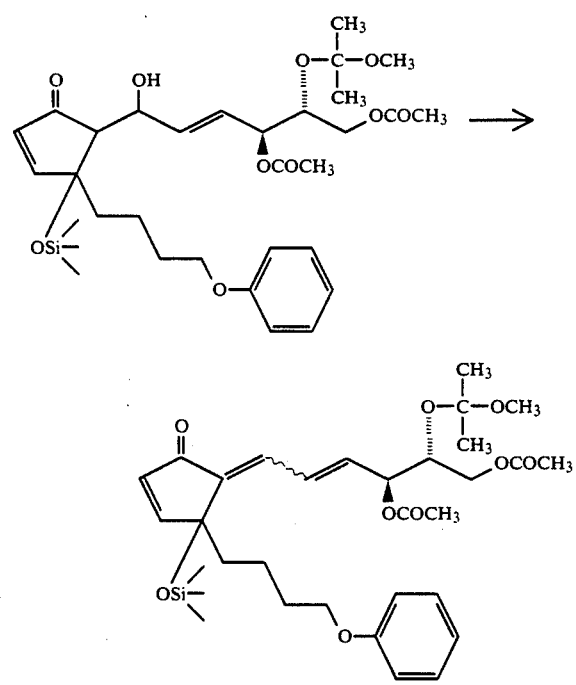

Triethylamine (2.2 ml) was added to 6 ml of a methylene chloride solution of 1.22 9 (1.96 mmoles) of the aldol product obtained in Example 1. The mixture was cooled to 0° C., and 230 microliters (3 mmoles) of methanesulfonyl chloride was added. The mixture was stirred for 10 hours. The temperature of the reaction mixture was returned to room temperature, and 488 m9 (4 mmoles) of dimethylaminopyridine was added, and the mixture was stirred for 2 hours. The reaction was terminated by adding water, and the reaction mixture was extracted with ether. The organic layer was washed with an aqueous potassium hydrogen sulfate solution, an aqueous sodium hydrogen carbonate solution and a saturated aqueous solution of sodium chloride in this sequence, and dried over anhydrous magnesium sulfate. The solvent was evaporated under reduced pressure, and the residue was subjected to Florisil column chromatography (hexane/ethyl acetate=10:1→3:1) to give 850 mg (72%) of a trienone compound.

NMR (δppm, CDCl$_3$): 1.4(s, 6H), 1.2–2.2(m, 6H), 2.1–2.2(sx3, total 6H), 3.3(s, 3H), 3.8–4.3(m, 5H), 5.7(m, 1H), 6.8–8.0(m, 10H).

EXAMPLE 3

Synthesis of 5-[(4S,5R)-4,6-diacetoxy-5-cyclopentenone

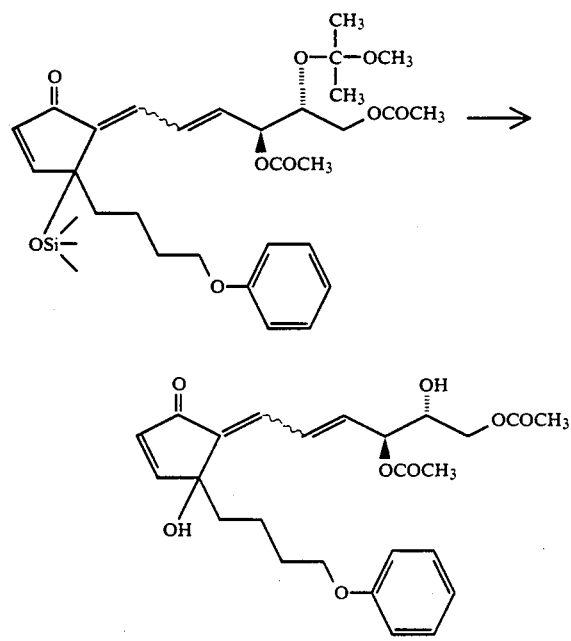

A solution (70 ml) of 789 mg (1.31 mmoles) of the trienone compound obtained in Example 2 in a mixture of acetic acid, water and tetrahydrofuran (3:1:1) was heated to 50° C., and stirred for 1 hour. Toluene was added and the reaction solution was evaporated. The residue was subjected to silica gel- column chromatography (hexane/ethyl acetate=1:2→1:4) to give 544 g (87%) of a diol compound.

IR (cm$^{-1}$, neat) 3400, 2950, 1740, 1690, 1640, 1500, 1370, 1240.

NMR (δppm, CDCl$_3$): 1.2-2.8(m, 8H), 2.1-2.2(sx3, total 6H), 3.8-4.3(m, 5H), 5.5(m, 1H), 6.0-8.0(m, 10H).

EXAMPLE 4

Synthesis of 5-(4S,5R)-4,5,6-trihydroxy-2-hexenylidene]-4-(4-phenoxybutyl)-4-hydroxy-2-cyclopentenone

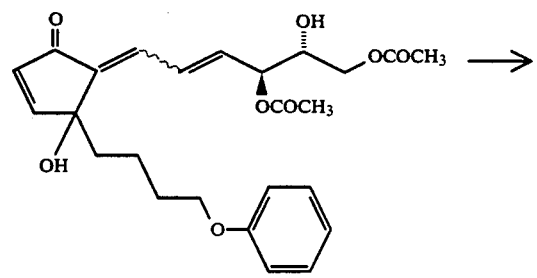

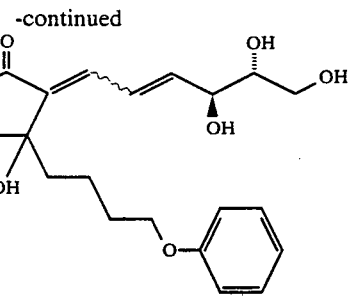

Fifty milliliters of 0.1M phosphate buffer (pH 8) and then 0.5 ml of porcine liver esterase (Sigma Co.) were added to 50 ml of an acetone solution of 207 mg (0.45 mmole) of the diacetate compound obtained in Example 3, and the mixture was stirred at room temperature for 3 days. The reaction mixture was saturated with ammonium sulfate, and extracted with ethyl acetate three times. The organic layers were washed with a saturated aqueous solution of sodium chloride, and dried over anhydrous magnesium sulfate. The solvent was evaporated under reduced pressure, and the residue was subjected to silica gel column chromatography (ethyl acetate→ethyl acetate, 5% methanol) to give 132 mg (78%) of a tetrol compound.

IR (cm$^{-1}$, neat) 3400, 2950, 1740, 1690, 1630, 1600, 1500, 1250.

NMR (δppm, CDCl$_3$): 1.1-2.6(m, 5H), 3.5-4.8(m, 10H), 6.1-8.0 (m, 10H).

EXAMPLE 5

Synthesis of 5-(4S,5R)-4,5,6-triacetoxy-2-hexenylidene-4-(4-phenoxybutyl)-4-hydroxy-2-cyclo-pentenone

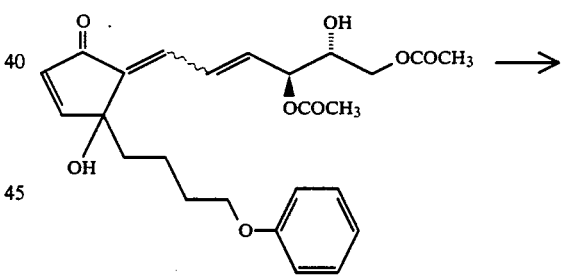

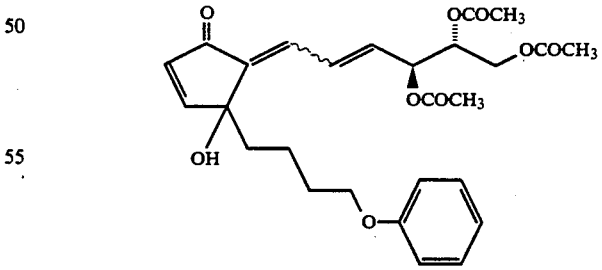

A toluene solution (2 ml) of 137 mg (0.3 mmole) of the diacetate compound obtained in Example 3 was cooled to 0° C., and 71 microliters (1 mmole) of acetyl chloride and then 81 microliters (1 ml) of pyridine were added. The mixture was stirred at 0° C. for 10 hours and the reaction was terminated by adding water. The reaction mixture was extracted with ethyl acetate. The organic layer was washed with an aqueous potassium hydrogen sulfate solution, an aqueous sodium hydrogen carbonate solution and a saturated aqueous sodium chloride solution in this sequence. The solvent was evaporated under reduced pressure. The resulting oily product was subjected to silica gel column chromatography (hexane:ethyl acetate=1:1→1:2) to give 116 mg (76%) of a triacetate compound.

IR (cm⁻¹, neat): 3450, 2950, 1740, 1690, 1640, 1600, 1500, 1370, 1240, 1220, 1040.

NMR (δppm, CDCl₃): 1.2-2.5(m, 6H), 2.0-2.1(sx3, total 9H), 3.8-4.3(m 4H), 5.25(m, 1H), 5.65(m, 1H), 5.9-8.0(m, 10H).

EXAMPLE 6

Synthesis of 5-[(4S,5R)-4,6-diacetoxy-1-hydroxy-5-(1-methoxy-1-methylethyloxy)-2-hexen-1-yl]-4-octyl-4-trimethylsilyloxy-2-cyclopentenone

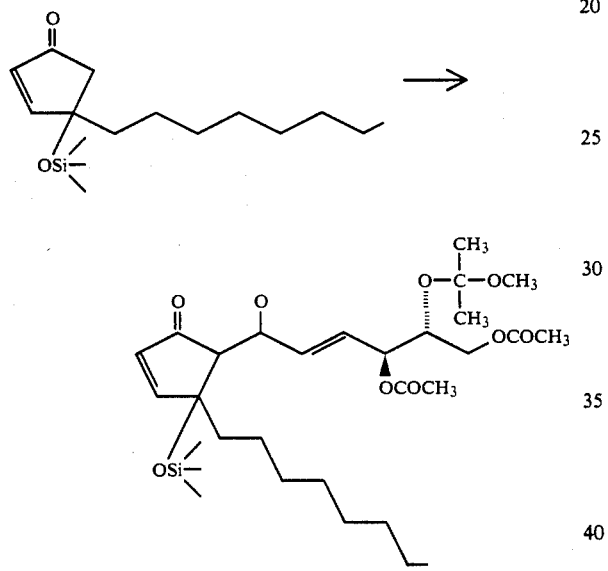

A solution composed of 1 g (3.55 mmoles) of 4-octyl-4-trimethylsilyloxy-2-cyclopentenone, 5 ml of dry hexane and 5 ml of dry ether was cooled to −78° C. under a nitrogen stream, and 870 microliters (5 mmoles) of diisopropylethylamine and then 4.6 ml (4.6 mmoles) of dibutylboron trifurate (1M CH₂Cl₂ solution) were added. The mixture was stirred at −78° C. for 1 hour. An ether solution (3 ml) of 1070 mg (3.55 mmoles) of (4S,5R)-4,6-diacetoxy-5-(1-methoxy-1-methylethyloxy)-2-hexenal was added, and the mixture was stirred for 2 hours. After the reaction, an aqueous solution of ammonium chloride was added to terminate the reaction, and the reaction mixture was extracted with ethyl acetate. The organic layer was washed with an aqueous potassium hydrogen sulfate solution, an aqueous sodium hydrogen carbonate solution and a saturated aqueous sodium chloride solution in this sequence, and dried over anhydrous magnesium sulfate solution. The solvent was evaporated under reduced pressure, and the resulting oily product was subjected to Florisil column chromatography (hexane:ethyl acetate: 5:1→3:1) to give 1.24 g (59%) of an aldol product.

NMR (δppm, CDCl₃): 0.8-2.2(m, 17H), 1.4(s, 6H), 2.1(s, 6H), 2.6(d, 1H, J=8.0Hz), 3.3(s, 3H), 4.0-4.3 (m, 3H), 4.6(m, 1), 5.6(m, 1H), 6.0(m, 2H), 6.25(d, 1H, J=6.0Hz), 7.70(d, 1H, J=6Hz).

EXAMPLE 7

Synthesis of 5-(4S,5R)-4,6-diacetoxy-5-(1-methoxy-1-methylethyloxy)-2-hexenylidene)-4-octyl-4-trimethylsilyloxy-2-cyclopentenone

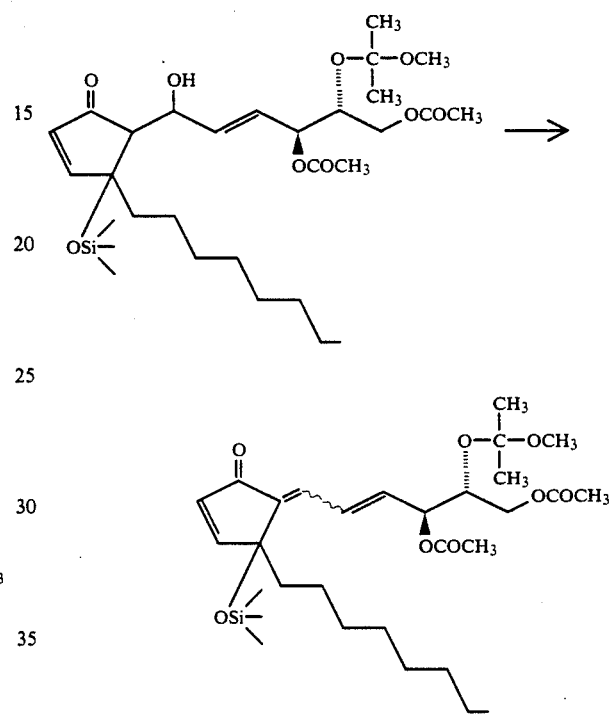

708 mg (5.8 mmoles) of 4-dimethylaminopyridine and then 235 microliters (3.04 mmoles) of methanesulfonyl chloride were added to 7 ml of a methylene chloride solution of 1.28 g (2.17 mmoles) of the aldol product obtained in Example 6, and the mixture was stirred at room temperature for 6 hours. Water was added to terminate the reaction, and the reaction mixture was extracted with ether. The organic layer was washed with an aqueous potassium hydrogen sulfate solution, an aqueous sodium hydrogen carbonate solution and a saturated aqueous sodium chloride solution in this sequence, and dried over anhydrous magnesium sulfate. The solvent was evaporated under reduced pressure, and the resulting oily product was subjected to Florisil column chromatography (hexane:ethyl acetate=10:1→3:1) to give 856 mg (69%) of a trienone compound.

NMR (δppm, CDCl₃): 1.4(s, 6H), 0.8-2.2(m, 17H), 2.1(s, 6H), 3.3(s, 3H), 4.0-4.3(m, 3H), 5.65(m, 1H), 6.0-8.0(m, 5H).

EXAMPLE 8

Synthesis of 5-(4S,5R)-4,6-diacetoxy-5-hydroxy-2-hexenylidene]-4-octyl-4-hydroxy-2-cyclopentenone

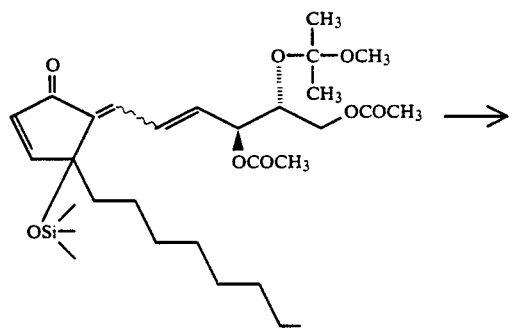

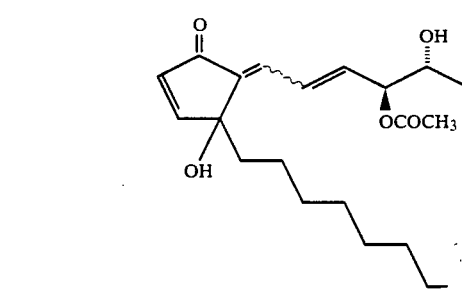

840 mg (1.47 mmoles) of the trienone compound obtained in Example 7 was dissolved in a mixture of acetic acid, tetrahydrofuran and water (3:1:1) to form 70 ml of a solution. The solution was heated to 50° C., and stirred. Toluene was put in the solution, and the reaction solution was evaporated. The residue was subjected to silica gel column chromatography (hexane:ethyl acetate=1:2→1:4) to give 510 mg (81%) of a diol compound.

NMR (δppm, CDCl₃): 0.8-2.2(m, 17H), 2.1-2.2(s, 6H), 4.0-4.3 (m, 3H), 5.5 (m, 1H), 6.0-8.0 (m, 5H).

EXAMPLE 9

Synthesis of 5-(4S,5R)-4,6-diacetoxy-1-hydroxy-5-(1-methoxy-1-methylethyloxy)-2-hexen-1-yl]-4-butyl-4-trimethylsilyloxy-2-cyclopentenone

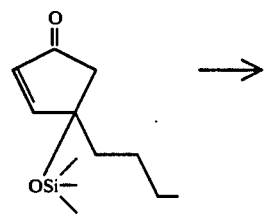

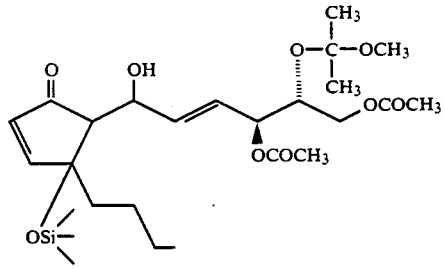

A solution composed of 904 mg (4 mmoles) of 4-butyl-4-trimethylsilyloxy-2-cyclopentenone, 6 ml of dry hexane and 6 ml of dry ether was cooled to −78° C. under a nitrogen stream, and 975 microliters (5.6 mmoles) of diisopropylethylamine and then 5.2 ml (5.2 mmoles) of dibutylboron trifurate (1M CH₂Cl₂ solution) were added. The mixture was stirred at −78° C. for 1 hour. An ether solution (4 ml) of 1210 mg (4 mmoles) of (4S,5R)-4,6-diacetoxy-5-(1-methoxy-1-methylethyloxy)-2-hexenal was added, and the mixture was stirred for 2 hours. An aqueous solution of ammonium chloride was added to terminate the reaction. The reaction mixture was extracted with ethyl acetate. The organic layer was washed with an aqueous potassium hydrogen sulfate solution, an aqueous sodium hydrogen carbonate solution and a saturated aqueous sodium chloride solution in this sequence, and dried over anhydrous magnesium sulfate. The solvent was evaporated under reduced pressure, and the resulting oily product was subjected to Florisil column chromatography (hexane:ethyl acetate=5:1→3:1) to give 1.16 g (55%) of an aldol product.

NMR (δppm, CDCl₃): 0.8-2.2(m, 9H), 1.4(s, 6H), 2.1(s, 6H), 2.65 (d, 1H, J=8.0Hz), 3.3(s, 3H), 4.0-4.3(m, 3H), 4.6(m, 1H), 5.6(m, 1H), 6.0(m, 2H), 6.2 (d, 1H, J=6.0Hz), 7.65(d, 1H, J=6.0Hz).

EXAMPLE 10

Synthesis of 5-(4S,5R)-4,6-diacetoxy-5-(1-methoxy-1-methylethyloxy)-2-hexenylidene)-4-butyl-4-trimethylsilyloxy-2-cyclopentenone

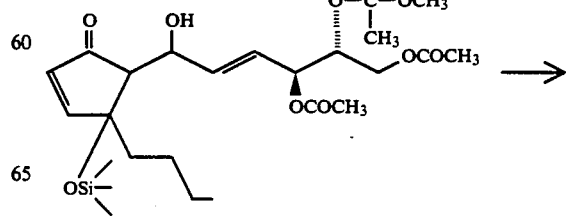

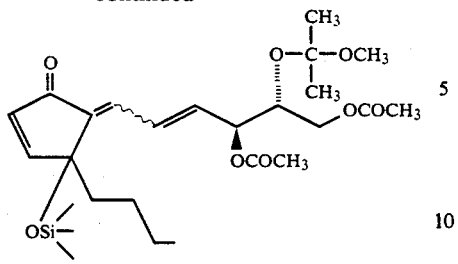

695 m9 (5.7 mmoles) of 4-dimethylaminopyridine and then 210 microliters (2.84 mmoles) of methanesulfonyl chloride were added to a methylene chloride solution (6 ml) of 1.0 g (1.89 mmoles) of the aldol product obtained in Example 9, and the mixture was stirred at room temperature for 8 hours. Water was added to terminate the reaction. The reaction mixture was extracted with ether. The organic layer was washed with an aqueous potassium hydrogen sulfate solution, an aqueous sodium hydrogen carbonate solution and a saturated aqueous sodium chloride solution in this sequence, and dried over anhydrous magnesium sulfate. The solvent was evaporated under reduced pressure, and the resulting oily product was subjected to Florisil column chromatography (hexane: ethyl acetate=10:1→3:1) to give 588 mg (61%) of a trienone compound.

NMR (δppm, CDCl₃): 1.4(s, 6H), 0.8–2.2(m, 9H), 2.1(s, 6H), 3.3(s, 3H), 4.0–4.35(m, 3H), 5.6(m, 1H), 5 6.0–8.0(m, 5H).

EXAMPLE 11

Synthesis of 5-(4S,5R)-4,6-diacetoxy-5-hydroxy-2-hexenylidene)-4-butyl-4-hydroxy-2-cyclopentenone

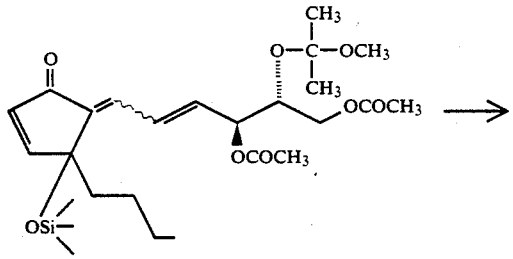

510 mg (1.0 mmole) of the trienone compound obtained in Example 10 was dissolved in a mixture of acetic acid, tetrahydrofuran and water (3:1:1) to form a solution (50 ml). The solution was heated to 50° C., and stirred. Toluene was put in the solution, and the reaction solution was evaporated. The residue was subjected to silica gel column chromatography (hexane:ethyl acetate=1:2→1:4) to give 285 mg (78%) of a diol compound.

NMR (δCDCl₃): 0.8–2.2(m, 9H), 2.1–2.2(s, 6H), 4.0–4.3(m, 3H), 5.5(m, 1H), 6.0–8.0(m, 5H).

EXAMPLE 12

Synthesis of 5-(4S,5R)-4,6-diacetoxy-1-hydroxy-5-(1-methoxy-1-methylethyloxy)-2-hexen-1-yl]-4-(3,4-dimethoxyphenylpropyl)-4-trimethylsilyloxy-2-cyclopentenone A solution composed of 1,04 g (3 mmoles) of 4-(3,4-dimethoxyphenylpropyl)-4-trimethylsilyloxy-2-cyclopentenone, 5 ml of dry hexane and 5 ml of dry ether was cooled to −78° C. under a nitrogen stream. To the solution were added 732 microliters (4.2 mmoles) of diisopropylethylamine and then 3.9 ml (3.9 mmoles) of dibutylborn trifurate (1M CH₂Cl₂ solution), and the mixture was stirred at −78 1 hour. Then, 4 ml of an ether solution of 906 mg (3 mmoles) of (4S,5R)-4,6-diacetoxy-5-(1-methoxy-1-methylethyloxy)-2-hexenal was added, and the mixture was stirred for 2 hours. After the reaction, an aqueous solution of ammonium chloride was added to terminate the reaction. The reaction mixture was extracted with ethyl acetate. The organic layer was washed with an aqueous potassium hydrogen sulfate solution, an aqueous sodium hydrogen carbonate solution, and a saturated aqueous sodium chloride solution in this sequence, and dried over anhydrous magnesium sulfate. The solvent was evaporated under reduced pressure, and the resulting oily product was subjected to Florisil column chromatography (hexane:ethyl acetate=5:1→3:1) to give 1.29 g (66%) of an aldol product.

NMR (δppm, CDCl₃): 1.4(s, 6H0, 1.4–1.9 (m, 4H), 2.1(s, 6H), 2.4–2.7(m, 3H), 3.3(s, 3H0, 3.80(s, 6H0, 4.0–4.3(m, 3H), 4.6(m, 1H), 5.6(m, 1H0, 6.0 (m, 2H), 6.2(d, 1H, J=6.0Hz), 614–6.9 (m, 3H), 7.77(d, 1H, J=6.0Hz).

EXAMPLE 13

Synthesis of
5-[(4S,5R)-4,6-diacetoxy-5-(1-methoxy-1-methoxyethyloxy)-2-hexenylidene]-4-(3,4-dimethoxyphenylpropyl)-4-trimethylsilyloxy-2-cyclopentenone

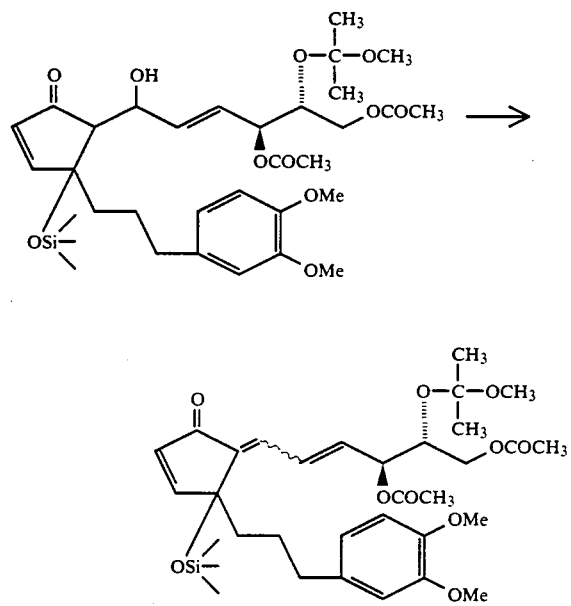

To 6 ml of a methylene chloride solution of 1.27 g (1.95 mmoles) of the aldol product obtained in Example 12 were added 714 mg (5.85 mmoles) of 4-dimethylaminopyridine and then 227 microliters (2.93 mmoles) of methanesulfonyl chloride, and the mixture was stirred at room temperature for 6 hours. Water was added to terminate the reaction, and the reaction mixture was extracted with ether. The organic layer was washed with an aqueous potassium hydrogen sulfate solution, an aqueous sodium hydrogen carbonate solution and a saturated aqueous sodium chloride solution in this sequence, and dried over anhydrous magnesium sulfate. The solvent was evaporated under reduced pressure, and the resulting oily product was subjected to Florisil column chromatography (hexane:ethyl acetate = 10:1→3:1) to give 924 mg (75%) of a trienone compound.

NMR (δppm, CDCl₃): 1.4(s, 6H), 1.4-1.9(m, 4H), 2.1(s, 6H), 2.4-2.7(m, 2H), 3.3(s, 3H), 3.8(s, 6H), 4.0-4.3(m, 3H), 5.65(m, 1H), 6.0-8.0(m, 8H).

EXAMPLE 14

Synthesis of
5-(4S,5R)-4,6-diacetoxy-5-hydroxy-2-hexenylidene)-4-(3,4-dimethoxyphenylpropyl)-hydroxy-2-cyclopentenone

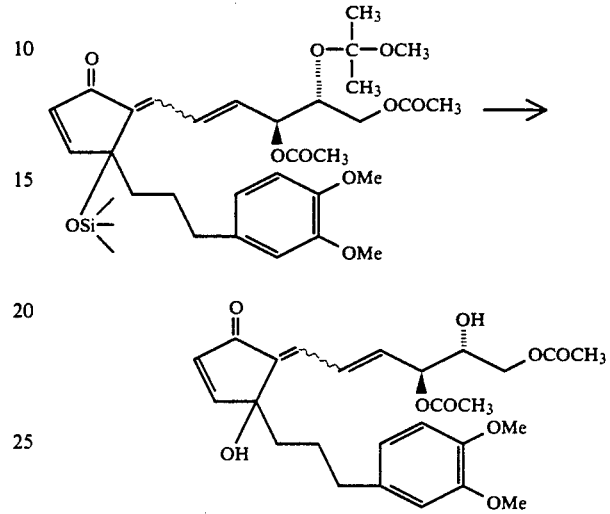

A solution (70 ml) of 810 mg (1.28 mmoles) of the trienone compound obtained in Example 13 in a mixture of acetic acid, tetrahydrofuran and water (3:1:1) was heated to 50° C., and the solution was stirred. Toluene was put in the solution, and the reaction solution was evaporated. The residue was subjected to silica gel column chromatography (hexane:ethyl acetate = 1:2→1:4) to give 481 mg (77%) of a diol compound.

NMR (δppm, CDCl₃): 1.4-1.9(m, 4H), 2.1-2.2(s, 6H), 2.4-2.7(m, 2H), 3.8(s, 6H), 5.5(m, 1H), 4.0-4.3(m, 3H), 6.0-8.0 (m, 8H).

EXAMPLE 15

Synthesis of
5-[(4S,5R)-4,5,6-trihydroxy-2-hexenylidene]-4-(3,4-dimethoxyphenylpropyl)-4-hydroxy-2-cyclopentenone

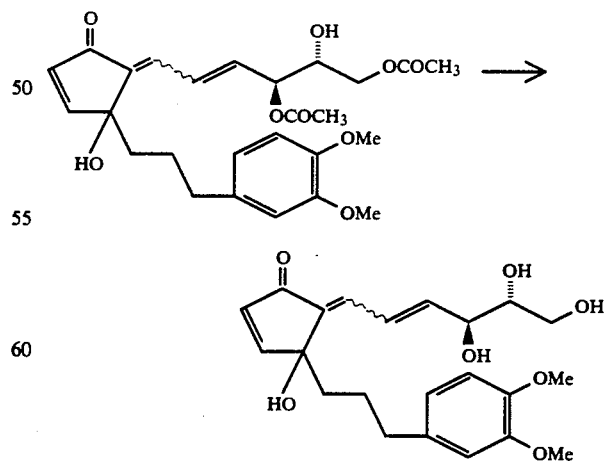

Fifty milliliters of 0.1M phosphate buffer (pH and then 0.5 ml of porcine liver esterase (Sigma Co.) were added to 5 ml of an acetone solution of 210 mg (0.43 mmole) of the diacetate obtained in Example 14, and the mixture was stirred at room temperature for 2 days.

The reaction mixture was saturated with ammonium sulfate, and extracted with ethyl acetate three times. The organic layers were washed with a saturated aqueous solution of sodium chloride, and dried over anhydrous magnesium sulfate. The solvent was evaporated under reduced pressure. The residue was subjected to silica gel column chromatography (ethyl acetate→ethyl acetate, 5% methanol) to give 98 mg (71%) of a tetraol compound.

NMR (δppm, CDCl$_3$): 1.3-1.9(m, 4H), 2.4-2.7(m, 2H), 3.8(s, 6H), 3.5-4.6(m, 8H), 6.1-8.0(m, 8H).

EXAMPLE A

Production of soft capsules 1 mg of the compound of Example 4 was dissolved in 60 g of fractionated coconut oil and soft capsules were produced by use of a soft gelatin capsule making machine, each capsule being made to contain 1 μg of the compound of Example 4.

EXAMPLE B

Production of powder

A powder was prepared in accordance with the following formulation.

| Active ingredient | 10 μg |
| --- | --- |
| Lactose | 100 mg |
| Corn starch | 100 mg |
| Hydroxypropyl cellulose | 10 mg |
| | 210 mg |

The active ingredient, lactose and corn starch were mixed, and an aqueous solution of hydroxypropyl cellulose was added. The mixture was dried to form a dust powder.

The compound of Example 4 was used typically as the active ingredient.

We claim:

1. A 2-cyclopentenone derivative represented by the following formula

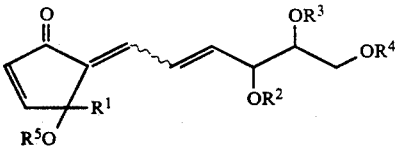

wherein $R^1$ represents an alkyl group having 1 to 10 carbon atoms which may be substituted by a substituted or unsubstituted phenyl or phenoxy group, $R^2$, $R^3$, $R^4$ and $R^5$ are identical or different and each represents a hydrogen atom or an alkanoyl group of up to 5 carbon atoms, and the wavy line shows that the bonded state of the double bond is E or Z.

2. The compound of claim 1 in which $R^1$ represents an alkyl group having 3 to 8 carbon atoms which may be substituted by a phenyl or phenoxy group which in turn may be substituted by 1 or 2 substituents selected from lower alkyl groups of up to 10 carbon atoms and lower alkoxy groups of up to 10 carbon atoms.

3. The compound of claim 1 in which $R^1$ represents a phenoxybutyl group.

4. A compound represented by the following formula:

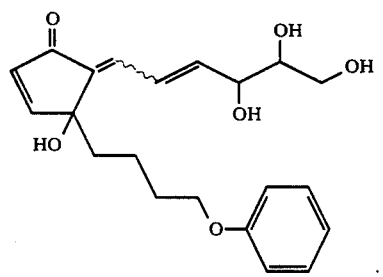

5. A compound represented by the following formula:

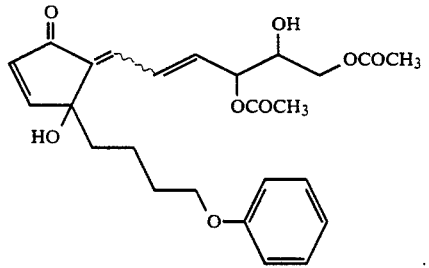

6. A pharmaceutical composition for the treatment of malignant tumors comprising a pharmaceutically effective amount of a 2-cyclopentenone derivative of claim 1, and a pharmaceutically acceptable carrier or diluent.

7. A method of treating malignant tumors which comprises administering a pharmaceutically effective amount of a 2-cyclopentenone derivative of claim 1 to a patient.

* * * * *